United States Patent
Lee et al.

(10) Patent No.: US 9,675,278 B2
(45) Date of Patent: Jun. 13, 2017

(54) BODY REHABILITATION SENSING METHOD BASED ON A MOBILE COMMUNICATION DEVICE AND A SYSTEM THEREOF

(71) Applicant: YUAN ZE UNIVERSITY, Taoyuan (TW)

(72) Inventors: Chien-Cheng Lee, New Taipei (TW); Chia-Hao Chang, Changhua County (TW)

(73) Assignee: YUAN ZE UNIVERSITY, Taoyuan (TW)

( * ) Notice: Subject to any disclaimer, the term of this patent is extended or adjusted under 35 U.S.C. 154(b) by 0 days.

(21) Appl. No.: 14/732,820

(22) Filed: Jun. 8, 2015

(65) Prior Publication Data
US 2016/0301792 A1 Oct. 13, 2016

(30) Foreign Application Priority Data
Apr. 7, 2015 (TW) .............................. 104111096 A

(51) Int. Cl.
*H04W 24/10* (2009.01)
*A61B 5/11* (2006.01)
(Continued)

(52) U.S. Cl.
CPC .............. *A61B 5/11* (2013.01); *A61B 5/0004* (2013.01); *A61B 5/6824* (2013.01);
(Continued)

(58) Field of Classification Search
USPC ........................................................ 455/702
See application file for complete search history.

(56) References Cited

U.S. PATENT DOCUMENTS

| | | | |
|---|---|---|---|
| 2014/0277582 A1* | 9/2014 | Leuthardt | A61F 2/72 623/25 |
| 2014/0336947 A1* | 11/2014 | Walke | A61B 90/98 702/19 |
| 2015/0133206 A1* | 5/2015 | Sarrafzadeh | A63F 13/235 463/7 |

FOREIGN PATENT DOCUMENTS

| | | |
|---|---|---|
| CN | 202761280 U | 3/2013 |
| TW | I377055 B | 11/2012 |

* cited by examiner

*Primary Examiner* — Vladimir Magloire
*Assistant Examiner* — Randy Peaches
(74) *Attorney, Agent, or Firm* — Li & Cai Intellectual Property (USA) Office

(57) ABSTRACT

The present disclosure provides a body rehabilitation sensing method based on a mobile communication device. The method comprises placing the mobile communication device at a specific portion of the limb of a user; a sensing module of the mobile communication device sensing the acceleration of the mobile communication device for generating an acceleration information; the mobile communication device transmitting the acceleration information to a remote server through a wireless network module; a computing module of the remote server analyzing the acceleration information and comparing the similarity of the acceleration information and a standard movement information; and the remote server transmitting the compare result of the similarity of the acceleration information and the standard movement information to the mobile communication device through the wireless network module. Accordingly, the user of the mobile communication device can acquire correctness of rehabilitation movements.

10 Claims, 13 Drawing Sheets

(51) Int. Cl.
    *A61B 5/00*         (2006.01)
    *H04W 4/02*      (2009.01)
    *H04W 4/00*      (2009.01)

(52) U.S. Cl.
    CPC .......... *A61B 5/6828* (2013.01); *A61B 5/6898* (2013.01); *H04W 4/025* (2013.01); *A61B 5/742* (2013.01); *A61B 2505/09* (2013.01); *A61B 2562/0219* (2013.01); *H04W 4/006* (2013.01)

BODY REHABILITATION SENSING METHOD BASED ON A MOBILE COMMUNICATION DEVICE AND A SYSTEM THEREOF

BACKGROUND OF THE INVENTION

1. Field of the Invention

The instant disclosure relates to a body rehabilitation sensing method for medical use; in particular, to a body rehabilitation sensing method based on a mobile communication device and a system thereof.

2. Description of Related Art

The current rehabilitation treatment of the patient is usually planned by the doctor and physiotherapist. According to the rehabilitation plan, the patient goes to the healthcare facility to use the rehabilitation equipment for conducting rehabilitation treatment in the designated time. However, medical equipment for rehabilitation is often in short supply, such that patient's rehabilitation time may be wasted on waiting.

SUMMARY OF THE INVENTION

The object of the instant disclosure is to provide a body rehabilitation sensing method based on a mobile communication device and a system thereof. By utilizing the sensor and the wireless network function of the mobile communication device, it provides a method and system to use the mobile communication device to store and transmit related data in real time when the user is doing rehabilitation movements. And, by judging the similarity of the rehabilitation movement, the user can immediately learn the correctness of the rehabilitation movement, for conducting rehabilitation more efficiently.

In order to achieve the aforementioned objects, according to an embodiment of the instant disclosure a body rehabilitation sensing method based on a mobile communication device is provided. The method is used for the mobile communication device. The mobile communication device has a wireless network module and a sensing module. The method comprises placing the mobile communication device at a specific portion of the limb of a user; a sensing module of the mobile communication device sensing the acceleration of the mobile communication device for generating an acceleration information; the mobile communication device transmitting the acceleration information to a remote server through a wireless network module; a computing module of the remote server analyzing the acceleration information and comparing the similarity of the acceleration information and a standard movement information; and the remote server transmitting the compare result of the similarity of the acceleration information and the standard movement information to the mobile communication device through the wireless network module.

In order to achieve the aforementioned objects, according to an embodiment of the instant disclosure a body rehabilitation sensing system is provided. The system comprises a remote server and a plurality of mobile communication devices. The mobile communication device has a wireless network module and a sensing module. The communication device utilizes the wireless network module for connecting to the remote server through the network. The mobile communication device is placed at a specific portion of the limb of a user. The sensing module of the mobile communication device senses the acceleration of the mobile communication device for generating an acceleration information. The mobile communication device transmits the acceleration information to the remote server through the wireless network module. A computing module of the remote server analyzes the acceleration information and compares the similarity of the acceleration information and a standard movement information. The remote server transmits the compare result of the similarity of the acceleration information and the standard movement information to the mobile communication device through the wireless network module.

In summary, this instant disclosure provides a body rehabilitation sensing method based on a mobile communication device and a system thereof. The provided method and system can be used for telemedicine and home care, for the user to conduct rehabilitation treatment at any time and any place. The user can immediately acquire the accuracy of his or her movement for better rehabilitation effectiveness, without needing to conduct rehabilitation treatment at a particular time and a particular place. Further, the body rehabilitation sensing method and system based on a mobile communication device provided in this instant disclosure directly uses the mobile communication device to store and transmit the movement information (acceleration information) of the user, so as to obtain advantages of convenience and simplicity.

In order to further the understanding regarding the instant disclosure, the following embodiments are provided along with illustrations to facilitate the disclosure of the instant disclosure.

DETAILED DESCRIPTION OF THE PREFERRED EMBODIMENTS

The aforementioned illustrations and following detailed descriptions are exemplary for the purpose of further explaining the scope of the instant disclosure. Other objectives and advantages related to the instant disclosure will be illustrated in the subsequent descriptions and appended drawings.

Figure 1:
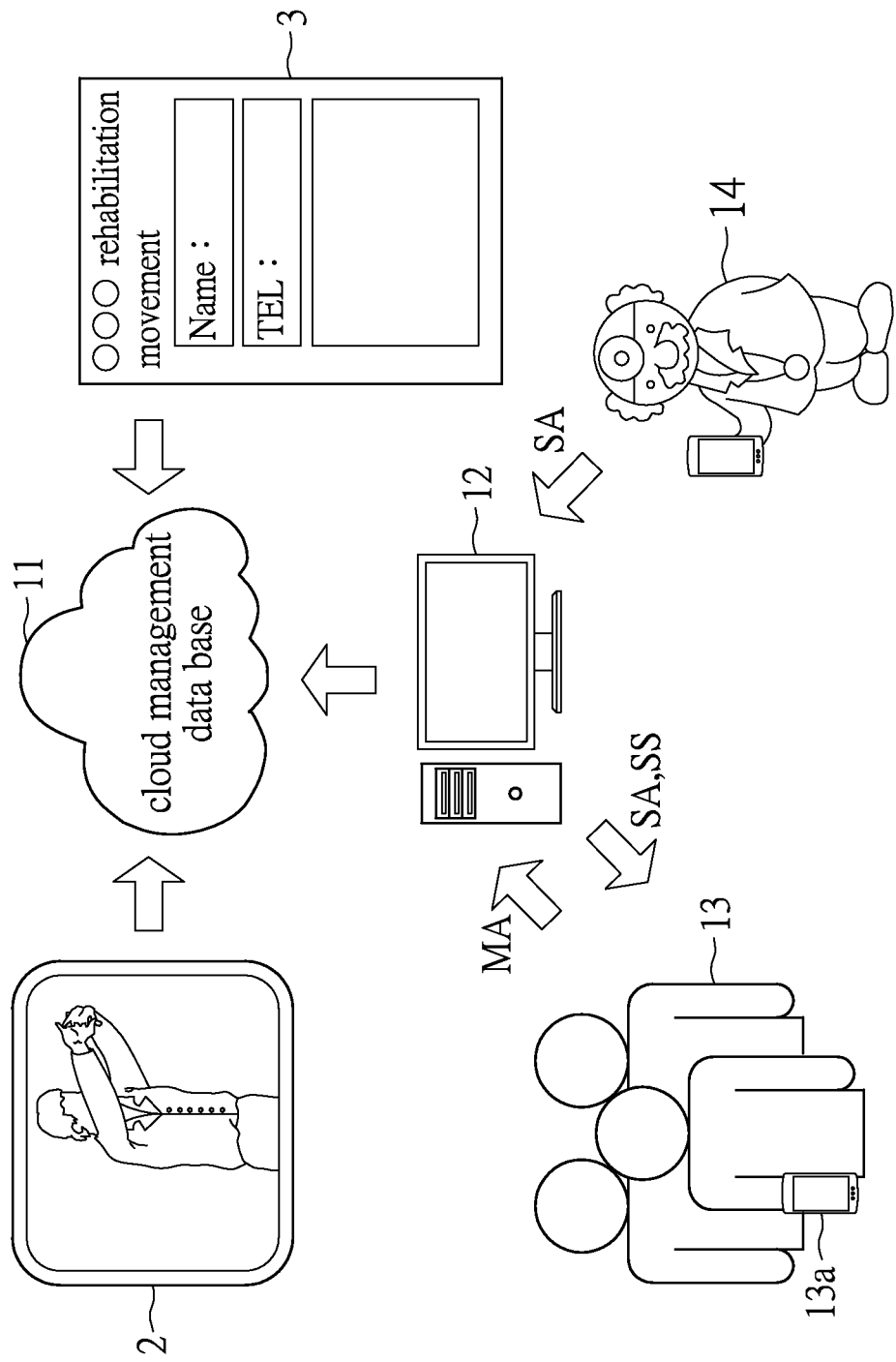
FIG. 1 shows an architecture diagram of a body rehabilitation sensing system based on a mobile communication device according to an embodiment of the instant disclosure.

Please refer to FIG. 1 showing an architecture diagram of a body rehabilitation sensing system based on a mobile communication device according to an embodiment of the instant disclosure. In this embodiment, the body rehabilitation sensing system comprises a remote server and a plurality of mobile communication devices. The remote server may not be a single server. The remote server can be a cloud server, or use big data server architecture. The communication device can be the smart phone widely used at present, but the instant disclosure is not so restricted. The mobile communication device can also be an easy to carry mobile communication device, such as a smart watch. As shown in FIG. 1, the remote server is illustrated as a server 12 and a cloud management database 11, but the instant disclosure is not so restricted. The remote server can be implemented by a variety of conventional network technologies.

The server 12 is connected with the cloud management database 11, in order to administer the cloud management database 11. The database stores standard movement information 2 related to a variety of body rehabilitation movements. Additionally, the database also stores body rehabilitation management information 3 in accordance with the rehabilitation treatments for all users, so as to manage the rehabilitation treatment by the medical institution. The standard movement information 2 can be stored in the form of video or image. For example, a video clip or a schematic diagram (or some schematic diagrams) demonstrating rehabilitation movement for the shoulder blade. The standard movement information 2 comprises body rehabilitation movements corresponding to a variety of rehabilitation treatments. The body rehabilitation management information 3 comprises medical records of the users (patients), types of body rehabilitation movements of rehabilitation treatments, rehabilitation time, and rehabilitation information . . . and so on. The body rehabilitation management information 3 is managed by the medical institution. For example, the doctor or the physiotherapist manages the rehabilitation treatment of the patients. After the patient sees the doctor, the hospital would provide the body rehabilitation management information 3 in accordance with the patient to the database (11). The content of the standard movement information 2 is designated or recorded by the doctor or the physiotherapist. The standard movement information 2 can be information pre-stored in the database, or the doctor (or the physiotherapist) can use the mobile communication device (a smart phone or a smart watch) or any other rehabilitation movement recording device to record a new video of the rehabilitation movement at any time, so as to establish a new standard movement information 2. Regarding how to establish the standard movement information 2 by using the mobile communication device, please refer to the descriptions about obtaining the acceleration information by the mobile communication device and analyzing the acceleration information which are explained later in this disclosure.

Each patient 13 can use his (or her) mobile communication device 13a to connect to the remote server (for example the server 12 shown in FIG. 1). The doctor 14 (or physiotherapist) can also use his (or her) mobile communication device whose function is similar to the mobile communication device 13a.

Figure 2:
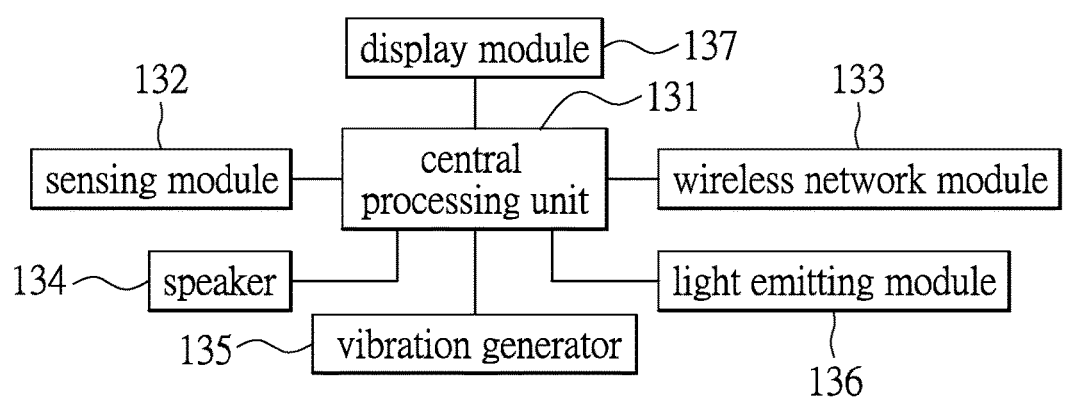
FIG. 2 shows a block diagram of a mobile communication device according to an embodiment of the instant disclosure.

Please refer to FIG. 1 in conjunction with FIG. 2. FIG. 2 shows a block diagram of a mobile communication device according to an embodiment of the instant disclosure. During the rehabilitation treatment, each patient 13 can use his (or her) mobile communication device 13a to sense the rehabilitation movement conducted by him (or her). Each mobile communication device 13a (smart phone or a smart watch for example) has a central processing unit 131, a sensing module 132, a wireless network module 133, a speaker 134, a vibration generator 135, a light emitting module 136, and a display module 137. The speaker 134, the vibration generator 135 and the light emitting module 136 are used to generate the indicating signal (whose application will be described later in this disclosure). The indicating signal can also be provided by the display module 137, therefore the speaker 134, the vibration generator 135 and the light emitting module 136 are not the necessary elements of the mobile communication device 13a. However, when using the smart phone as the mobile communication device 13a, it can be easily seen that most of the current smart phones have a speaker, a vibration generator, a light emitting module, and other components.

Figure 4:
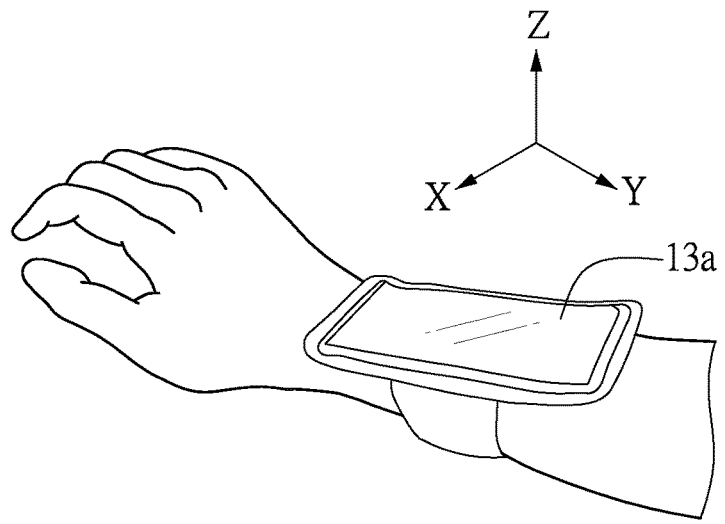
FIG. 4 shows a schematic diagram of a mobile communication device placed at a forearm of a user according to an embodiment of the instant disclosure.

The mobile communication device 13a can be a device belonging to the user (patient), so that medical institutions do not have to provide the mobile communication device 13a. The user can install a specific application (App, which is provided by the medical institution providing rehabilitation treatments) to the mobile communication device 13a to conduct sensing and connect to the remote server. Each communication device 13a utilizes the wireless network module 133 for connecting to the remote server through the network. For example, connecting to the server 12 shown in FIG. 1. The mentioned mobile communication device is placed at a specific portion of the limb of the user. The specific portion of the limb can be predetermined or defined in advance. For example, the specific portion can be determined by the content of the standard movement information. The specific portion of the limb can be the wrist, the forearm, the palm, the calf, and so on. As an example, FIG. 4 shows a mobile communication device placed at a forearm of the user. The user can use an auxiliary component such as a sleeve to fix the mobile communication device on the forearm of the user. However, the manner of fixing the mobile communication device at the specific portion of the user's limb is not so restricted. Another example can be the user griping the mobile communication device by his (or her) palm, the mobile communication device being placed on the calf by using the auxiliary component, or setting the mobile communication device on one shoe worn by the user, and so on.

The sensing module 132 of the mobile communication device 13a senses the acceleration of the mobile communication device 13a for generating an acceleration information MA. The mobile communication device 13a transmits the acceleration information MA to the remote server (such as the server 12 of FIG. 1) through the wireless network module 133.

The sensing module 132 can be a triaxial accelerometer, a gravity sensor or a gyroscope for example, but the instant disclosure is not restricted thereto.

A computing module of the remote server (such as the server 12 of FIG. 1) analyzes the acceleration information MA and compares the similarity of the acceleration information MA and a standard movement information SA. According to the architecture of the remote server, for example the cloud or big data analysis, the implementation of the remote server may be different. The computing module provided in this embodiment is a functional block providing the computing function, and is not limiting the hardware or software used to implement the computing module in practical applications.

In the following, the body rehabilitation sensing method based on the mobile communication device is described. Please refer to FIG. 1 in conjunction with FIG. 2 and FIG. 3A. The method comprising the following steps. Firstly, in step S110, placing the mobile communication device 13a at a specific portion of the limb of the user. Then, in step S120, the sensing module 132 of the mobile communication device 13a sensing the acceleration of the mobile communication device 13a for generating the acceleration information MA. Then, in step S130, the mobile communication device 13a transmitting the acceleration information MA to the remote server (such as the server 12 of FIG. 1) through the wireless network module 133. Then, in step S140, the computing module of the remote server analyzing the acceleration information MA and comparing the similarity of the acceleration information MA and the standard movement information SA. After step S140, go to step S150, the remote server transmitting the compare result SS of the similarity of the acceleration information MA and the standard movement information SA to the mobile communication device 13a through the wireless network module 133.

In one embodiment, the standard movement information SA can be recorded by the sensing module of the same mobile communication device (or by another mobile communication device having similar functions) in advance. The doctor (or the physiotherapist) can use a specific sensing device or his (or her) mobile communication device to connect to the remote server. The functions of the mentioned sensing device or the mobile communication device belonging to the doctor (or the physiotherapist) can be similar to the functions of the mobile communication device 13a belonging to the user. For example, the doctor (or the physiotherapist) can use his or hersmart phone to record the standard movement information SA, used for comparing with the rehabilitation movement of the user. The doctor (or the physiotherapist) can establish a new rehabilitation treatment at will, based on the necessity of the user's rehabilitation.

Figure 3A:
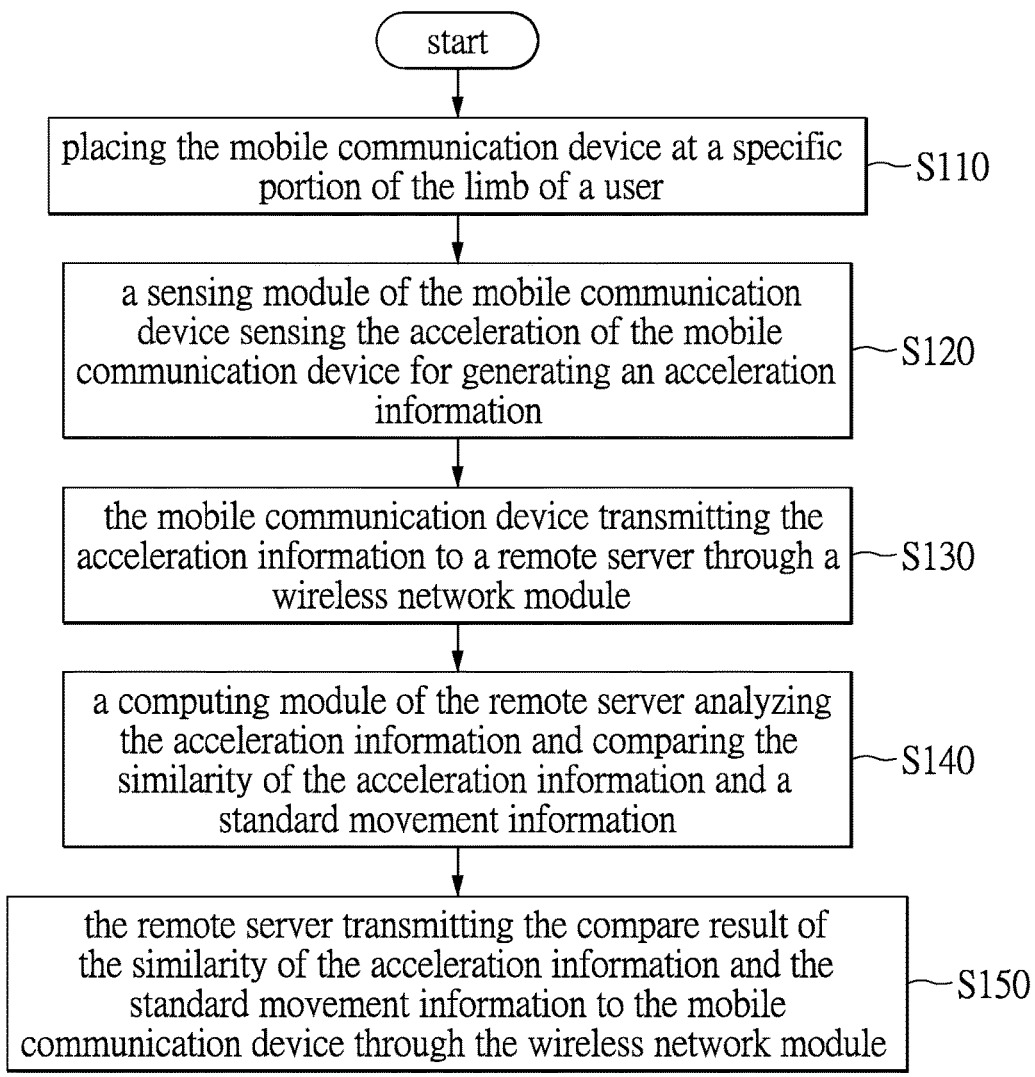
FIG. 3A shows a flow chart of a body rehabilitation sensing method based on a mobile communication device according to an embodiment of the instant disclosure.
Figure 3B:
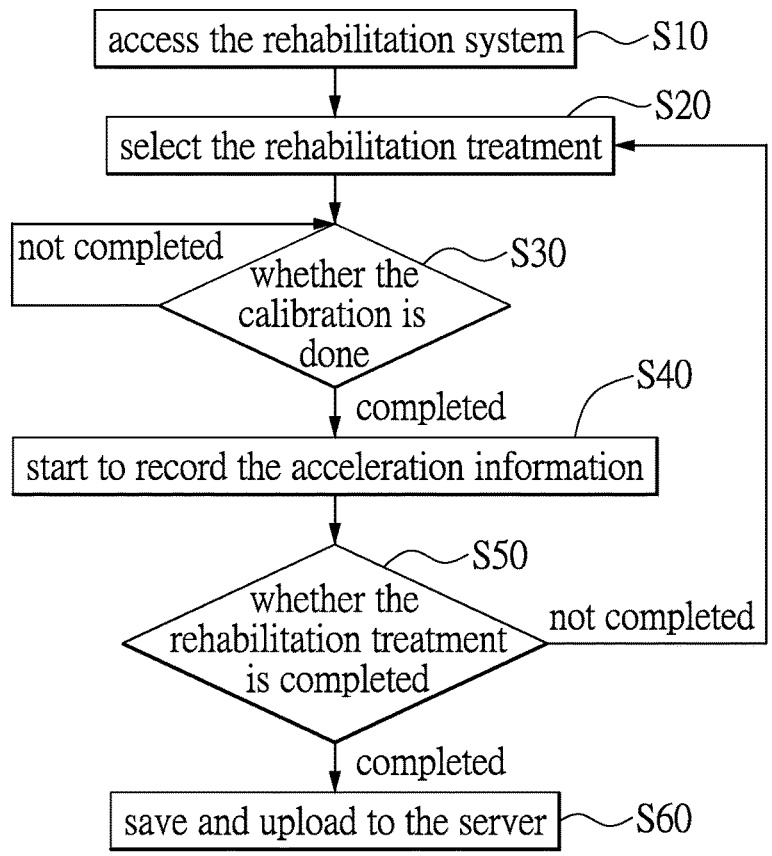
FIG. 3B shows a flow chart of a mobile communication device recording the body rehabilitation information according to an embodiment of the instant disclosure.
Figure 5A:
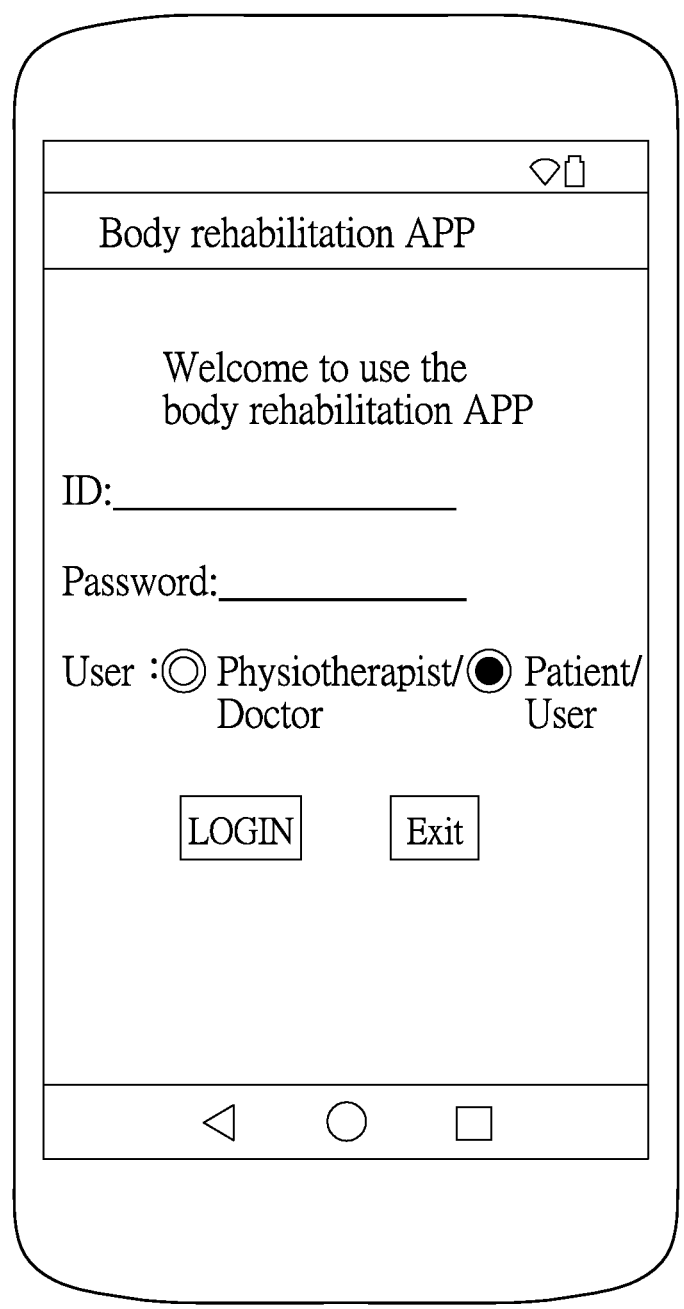
FIG. 5A shows a schematic diagram of a login interface of the body rehabilitation application of the mobile communication device according to an embodiment of the instant disclosure.
Figure 5B:
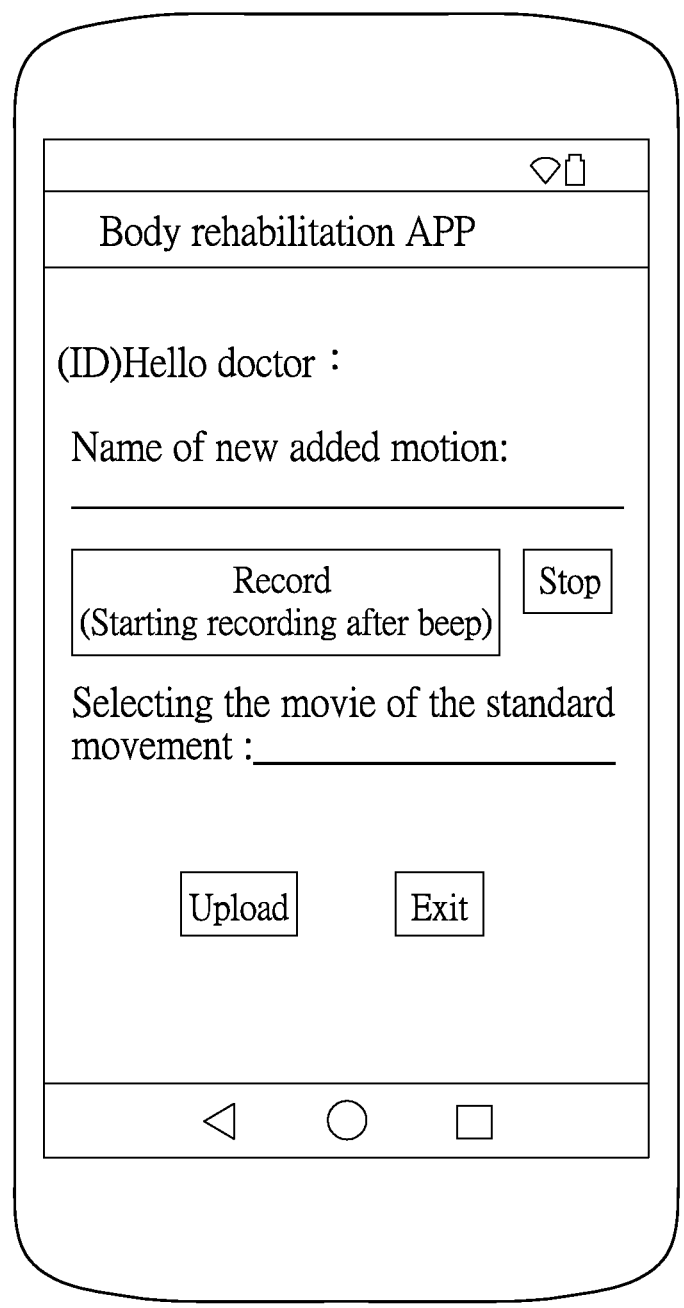
FIG. 5B shows a schematic diagram of a login interface of the body rehabilitation application of the mobile communication device according to an embodiment of the instant disclosure.
Figure 5C:
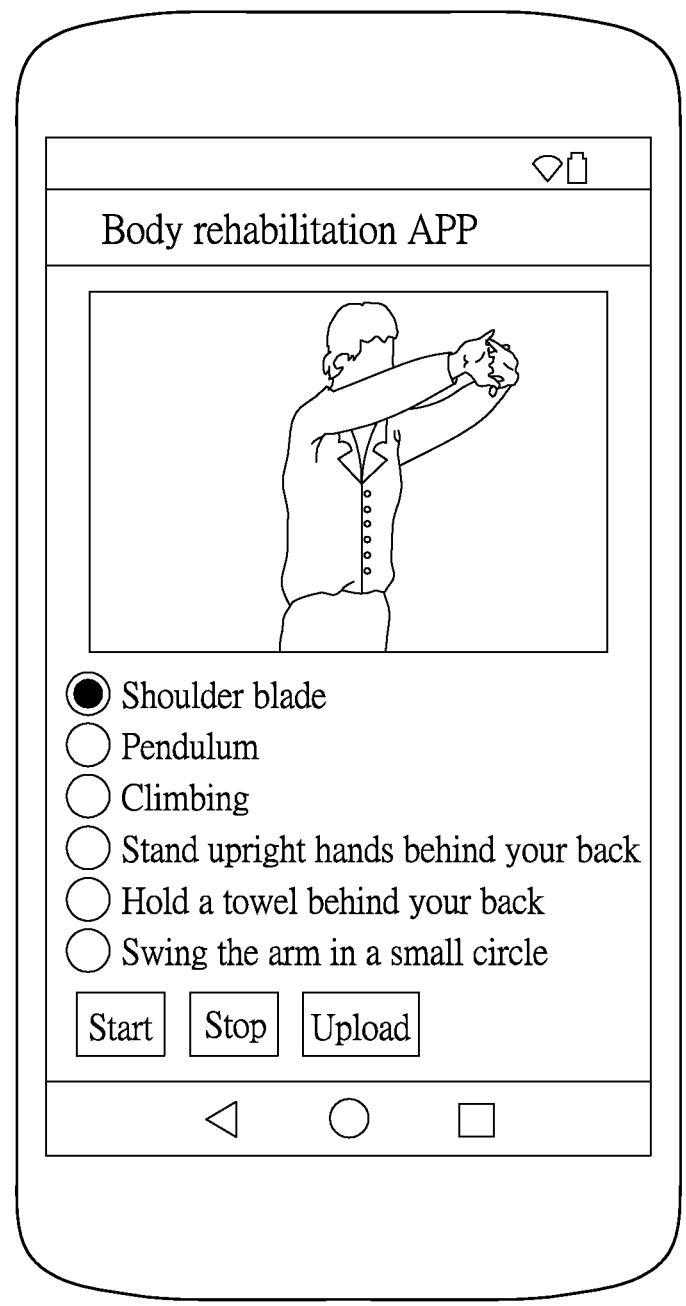
FIG. 5C shows a schematic diagram of a user interface of the body rehabilitation application of the mobile communication device according to an embodiment of the instant disclosure.

Based on the flow chart of FIG. 3, please refer to FIG. 3B, FIG. 5A, FIG. 5B, FIG. 5C and FIG. 5D, which further describes details of the method from the point of view of the mobile communication device (referred to as the mobile communication device 13a shown in FIG. 2). The steps S10, S20, S30, S40, S50 and S60 are executed by using the mobile communication device. Firstly, in step S10, the user using the mobile communication device to login in the rehabilitation system. As shown in FIG. 5A, a login interface of the body rehabilitation application is illustrated. The user can use the mobile communication device to login to the remote server. Further, the login interface shown in FIG. 5A can also be used to login by the physiotherapist or the doctor, for adding new rehabilitation movements. If the login person is the physiotherapist or the doctor, then entering the interface shown in FIG. 5B. The physiotherapist or the doctor can input the subject of a newly added movement, and use the mobile communication device to sense and record the standard movement information SA of the newly added movement, and then upload the new standard movement information SA to the remote server. Additionally, the physiotherapist or the doctor can input a video of the standard movement corresponding to the newly added standard movement, such that the user (patient) can watch the video to imitate the rehabilitation movement. If the login person is the user (patient), then go to step S20, the mobile communication device displays the interface shown in FIG. 5C, for the user to select the rehabilitation treatment. The user can select the treatment to be carried out and watch the video of the standard movement recorded in advance. After selecting the video and pressing the virtual start icon, the demo video would be displayed. After several seconds from the end of the video, the application would automatically instruct the user to start the rehabilitation. When the rehabilitation movement is completed, the user can press the upload icon, and then the application shows the interface shown in FIG. 5D for indicating the rehabilitation result rating. In other words, before the step S110 of FIG. 3A (placing the mobile communication device at a specific portion of the limb of the user), the method further comprises: the mobile communication device receives a rehabilitation movement information (including rehabilitation treatment, video of the standard movement, and so on) from the remote server through the wireless network module, and the mobile communication device displays the rehabilitation movement information by a display module of the mobile communication device.

Further, when the user places the mobile communication device at a specific portion of the limb indicated by the standard movement video, the mobile communication can conduct a sensing process. In step S30, the mobile communication device determines whether the calibration is done. Specifically, before the mobile communication device starts to sense, the mobile communication device corrects the sensed signals, in order to avoid sensing error. In other words, after the step S110 (placing the mobile communication device at the specific portion of the limb of the user), and before the step S120 (the sensing module of the mobile communication device sensing the acceleration of the mobile communication device for generating an acceleration information), the method further comprises: the sensing module of the mobile communication device executing a correction process. In one embodiment, the mentioned correction process is determining whether the acceleration of the mobile communication device sensed by the sensing module is less than a stability threshold for a time period. The mobile communication device can generate an indicating signal, wherein the indicating signal represents the mobile communication device is ready to sense the acceleration of the mobile communication device to generate the acceleration information. The indicating signal may be sounds generated by the speaker 134, vibrations generated by the vibration generator 135, emitted light or flash light generated by the light emitting module 136, or a display signal (image) displayed on the display module 137.

When the correction process is completed, then go to step S40; otherwise, redo the correction process again. In step S40, the mobile communication device starts to record the acceleration information, and the step S40 is in accordance with the step S120 shown in FIG. 3A. That is, the user imitates the standard movement to conduct the rehabilitation. Then, go to step S50, determining whether the rehabilitation treatment is completed. If the rehabilitation treatment is not completed yet (for example, the user's rehabilitation treatment comprises a plurality of rehabilitation movements), then go back to step S20, such that the user can select another rehabilitation treatment.

In one embodiment, by designing the application, the user can press the stop icon of the mobile communication device to stop recording the acceleration information when completing each rehabilitation treatment, then the user can press the upload icon (such the upload icon shown in FIG. 5C), such that the application can automatically upload the acceleration information to the remote server.

In another embodiment, the mobile communication device can be designed to actively sense whether the user's movement has stopped or not from the beginning to the end of sensing the acceleration of the mobile communication device, so as to determine whether the user has completed the rehabilitation treatment. In other words, after step S120 of FIG. 3A (the sensing module of the mobile communication device sensing the acceleration of the mobile communication device for generating an acceleration information), and before step S130 (the mobile communication device transmitting the acceleration information to a remote server through the wireless network module), the method further comprises: the mobile communication device generating an indicating signal for presenting the sensing status; the indicating signal reminding the user to decrease the speed of the movement of the limb when the sensing module senses the acceleration of the mobile communication device exceeds a threshold (which indicate the acceleration is too large, where it can lead to inaccurate sensing); and the indicating signal representing the completion of the body rehabilitation movement of the user when the sensing module senses the acceleration of the mobile communication device is less than a stability threshold for a time period (which represents the mobile communication device is almost not moving). The indicating signal can be sounds, vibrations, emitted light, flashing light, or a display signal (image) displayed on the display module of the mobile communication device.

Figure 5D:
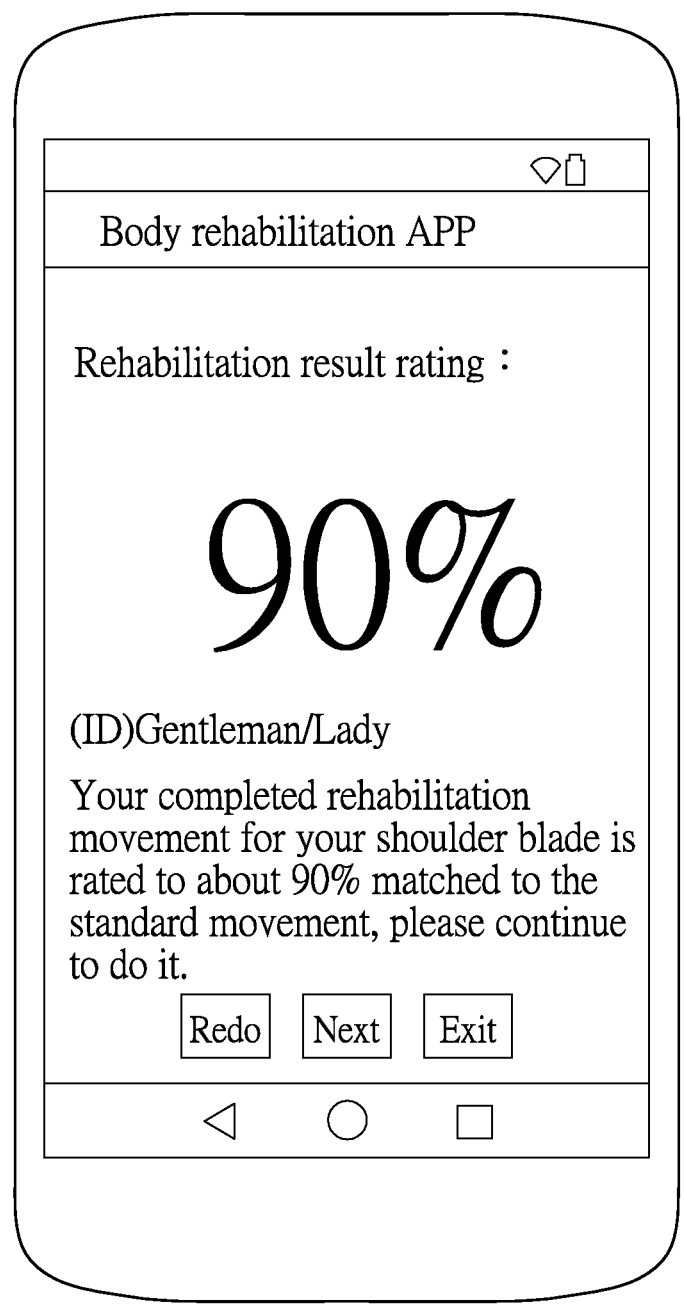
FIG. 5D shows a schematic diagram of an interface of effectiveness of rehabilitation for the body rehabilitation application of the mobile communication device according to an embodiment of the instant disclosure.

When the mobile communication device determines the rehabilitation treatment is completed (the limb has stopped moving), then go to step S60, saving and uploading the acceleration information to the server, which is the step S140 of FIG. 3A. After step S60 (after step S140), the step S150 of FIG. 3 enables the mobile communication device to receive and display the compare result of the similarity of the acceleration information MA and the standard movement information SA, as shown in FIG. 5D. The user can watch the content displayed by the mobile communication device to acquire the effectiveness of rehabilitation responding to the compare result. The effectiveness of rehabilitation can be the details of the similarity result and the corresponding rehabilitation medical knowledge. The content of the effectiveness of rehabilitation can be database links designed during the system design phase according to the professional medical knowledge of the physiotherapist or the doctor.

Figure 6:
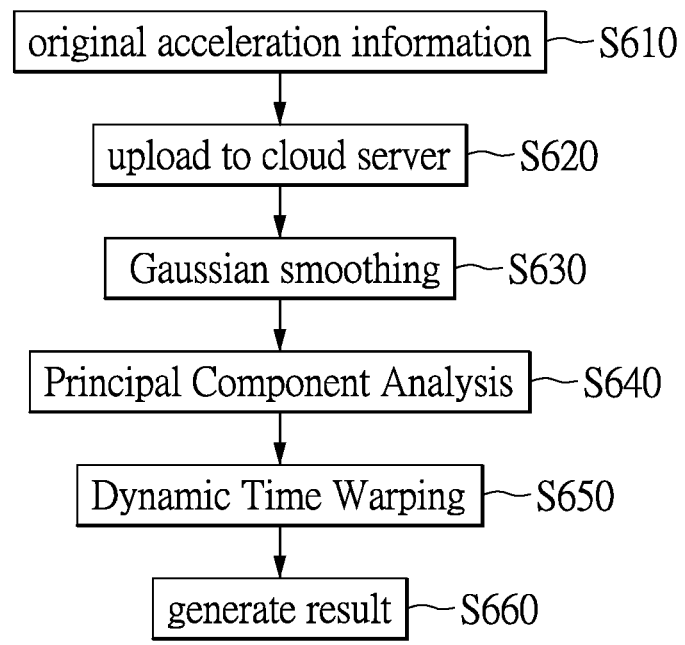
FIG. 6 shows a flow chart of analyzing the acceleration information according to an embodiment of the instant disclosure.

Then, please refer to FIG. 6 showing a flow chart analyzing the acceleration information according to an embodiment of the instant disclosure. At first, obtaining the original acceleration information (step S610). Then, uploading the acceleration information to the remote server (the cloud server for example) (step S620). The step S610 and the step S620 respectively correspond to the step S120 and the step S130 shown in FIG. 3A. The analysis process of the remote server is steps S630, S640, S650 and S660. The analysis process in this instant disclosure is for ease of explanation, and the mentioned algorithm is not used to limit the scope of this invention. In this embodiment, Gaussian smoothing is applied to the original three-axis acceleration signal. To obtain the invariant of the signal, principal component analysis (PCA) is used to obtain a principal axis, and then mapping the original three-axis signal to the principal axis, such that the signal is invariant in the three dimension space. Finally, using dynamic time warping (DTW) to measure the similarity between two different three-axis acceleration sequences by Euclidean distance.

Specifically, in step S630, performing Gaussian smoothing. The Gaussian smoothing filter is a linear smoothing filter whose weights are selected by the shape of the Gaussian function. In this embodiment, a normal distribution with an average value $\mu$, and a standard deviation $\sigma$, $X \sim N(\mu, \sigma^2)$ is used, and the probability density function is $$f(x) = \frac{1}{\sigma\sqrt{2\pi}} e^{\frac{-(x-\mu)^2}{2\sigma^2}}.$$

Figure 7A:
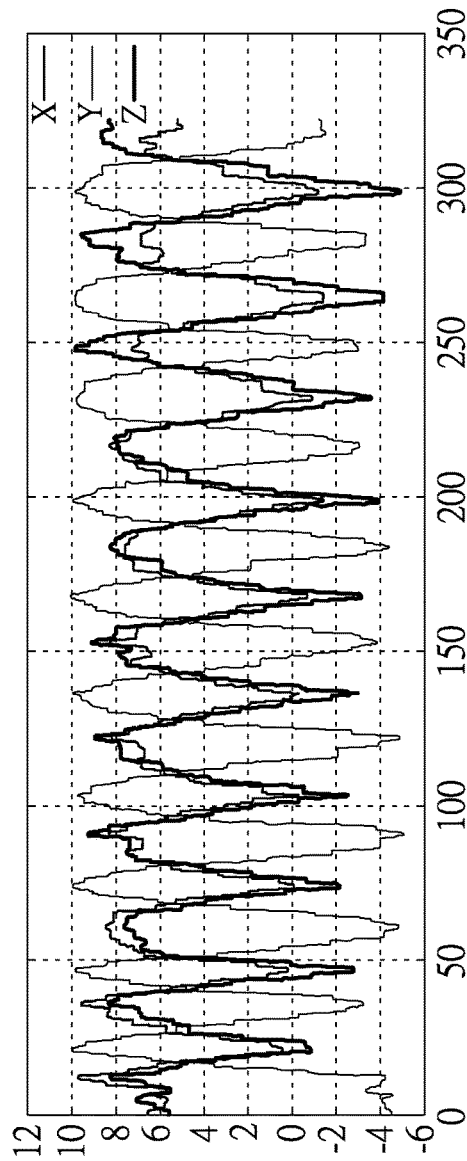
FIG. 7A shows a schematic diagram of the components in X, Y, Z axes of the original acceleration signal according to an embodiment of the instant disclosure.
Figure 7B:
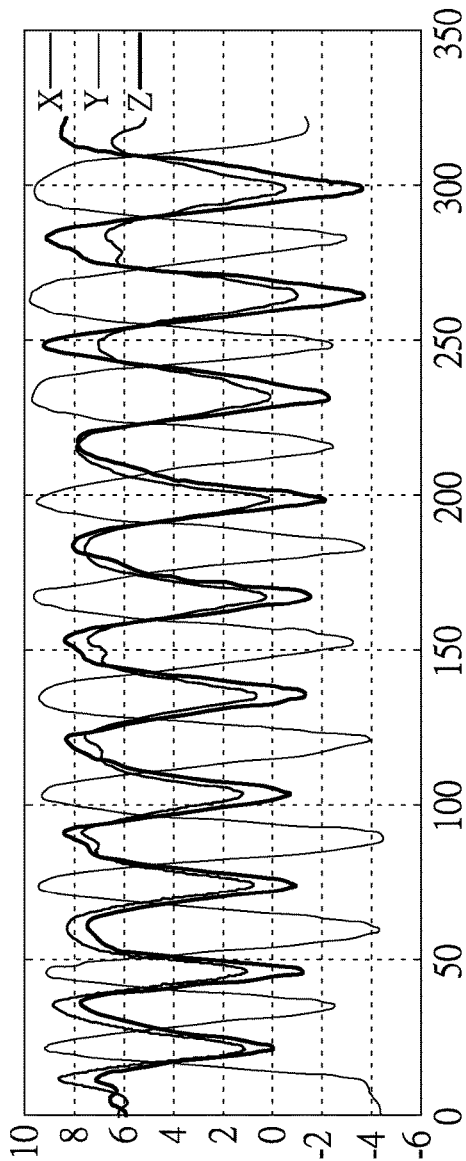
FIG. 7B shows a schematic diagram of the acceleration signal shown in FIG. 7A after applying Gaussian smoothing.
Figure 7C:
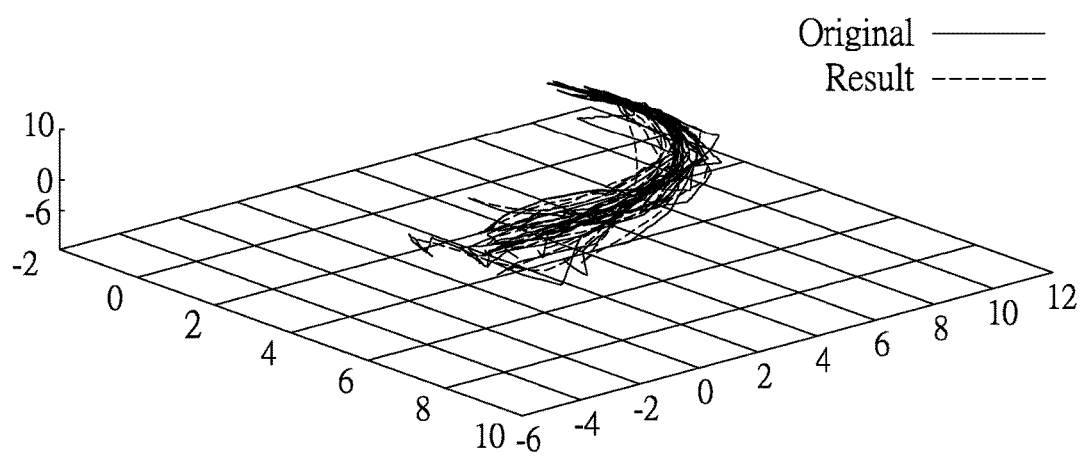
FIG. 7C shows a schematic diagram of the acceleration signals shown in FIG. 7A and FIG. 7B presented in three-dimensional space.

When the kernel density used is 9, the integrity of the original signal is retained when smoothing the kernel density, as shown in FIG. 7A and FIG. 7B (in this example the rehabilitation movement is shoulder blade movement). FIG. 7C also shows that the original acceleration signal and the smoothed acceleration signal are almost overlapped in three dimensions, that is, these two signals do not have a substantial difference.

Then, executing step S640, performing principal component analysis. Principal component analysis which originated from statistics is a concept of data sets, and is a linear transformation transferring the data to a new coordinate, such that a first maximum variance of the mapped data is located in a first coordinate, and a second maximum variance of the mapped data is located in a second coordinate. A few principal components can recover the original data set by using linear combination. In short, the principal component analysis decreases dimensions of the data while retaining the most significant feature of the data. The low order principal components are retained, and high order principal components are ignored, wherein the lower principal components can retain the most important portion of the data. The principal component analysis finds out the direction of the largest variance, and intends to explain most variation situations of the original data by using least variances. Arie et al. provide a three-dimensional (3D) space normalization method (referring to D. Vranic and D. Saupe. "3D shape descriptor based on 3D fourier transform," pp. 271-274, Budapest, Hungary, 2001; and D. V. Vranic, D. Saupe, and J. Richter, and "Tools for 3D-object retrieval: Karhune-loeve transform and spherical harmonics," appearing in IEEE Workshop on Multimedia Signal Processing (MMSP'2001), Cannes, France, 2001) to define a normalized coordinate, and map the three-axis trace to the principal axis in each direction, by using principal component analysis, such the trace in three dimensional space can have rotation invariance and translation invariance.

If $P=\{P_1, P_2, \ldots, P_n\}(P_i=(x_i, y_i, z_i)\in R^3)$, $\emptyset$ is supposed to be found out, $\emptyset$ makes the trace data retain the invariant specificity, wherein $\emptyset$ satisfies the equation as follows, $\tau(I)=\tau(\emptyset(I)), \emptyset(I):=\{\emptyset(v)|v\in I\}$, $S=S_1+\ldots+S_m=\int_I dv$.

Figure 8:
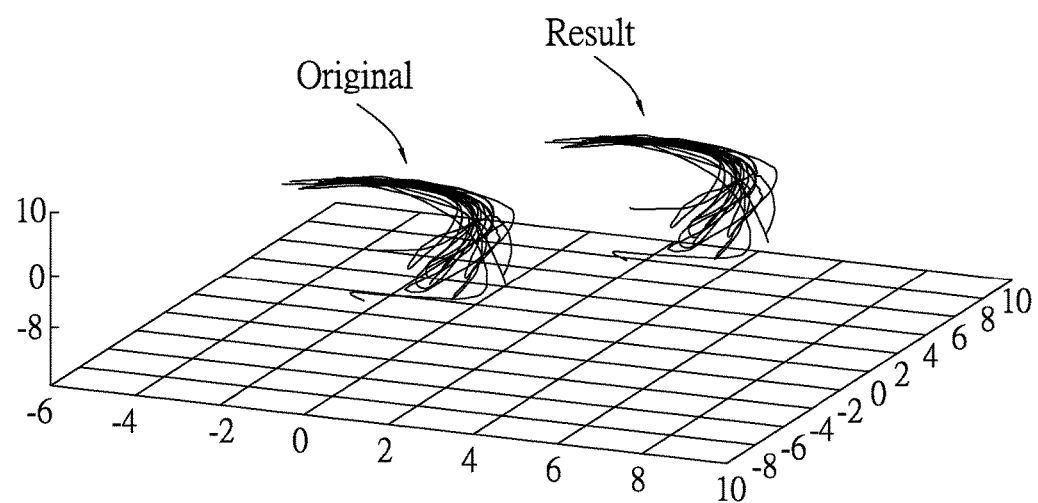
FIG. 8 shows a schematic diagram of the original acceleration signal and the translated acceleration signal in three-dimensional space.

Translation invariance: translating each point to the center of the trace (as shown in FIG. 8) by the following equation:

$$c = S^{-1} \iint_I v \, ds (v \in I).$$

It can be seen $I'=u|u=v-c, v\in I$.

Figure 9:
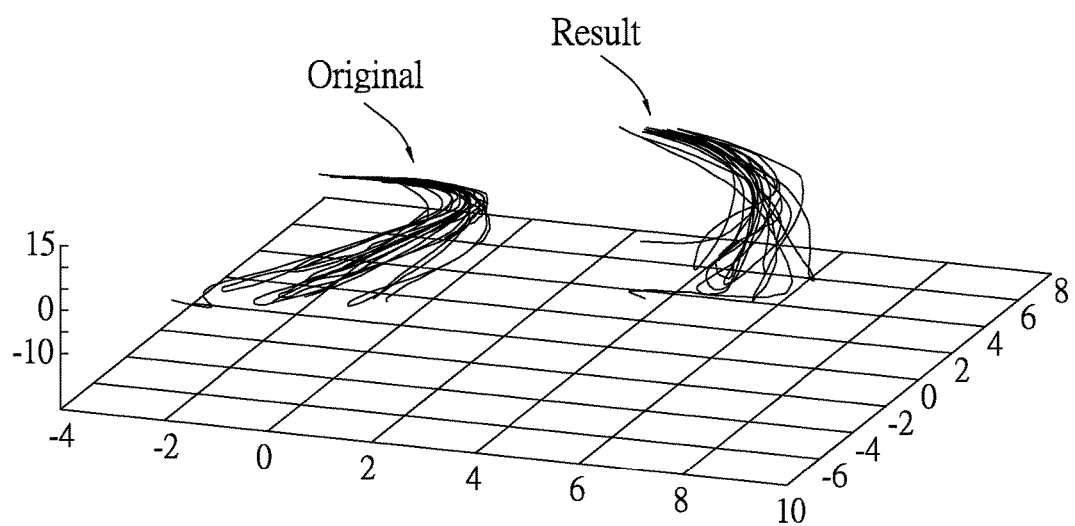
FIG. 9 shows a schematic diagram of the original acceleration signal and the rotated acceleration signal in three-dimensional space.

Rotation invariance: referring to FIG. 9, obtaining a rotation matrix R by calculating a covariance matrix of a diagonal matrix $$M = \frac{1}{S} \int_{I1} v \cdot v^T,$$

and arranging the eigenvalues in descending order. Then, $I_2$ can be obtained.

Then, executing step S650, performing dynamic time warping. Dynamic time warping is a conventional algorithm common used in speech recognition. This algorithm is originated from dynamic programming (DP) which solves the problem of time inconsistence of event sequences for speech recognition.

For speech recognition, the speaking speed of each person is not the same, but expressing the same meaning. It is similar to rehabilitation movement recognition. Even if each person performs the movement in the same way as he or she can, the speed of the movement may be different, and the length of time sequences changes accordingly. However, the traces of the movements are similar. Dynamic time warping is used to correct the time sequence, and find out the most matching trace between two movements.

Figure 10:
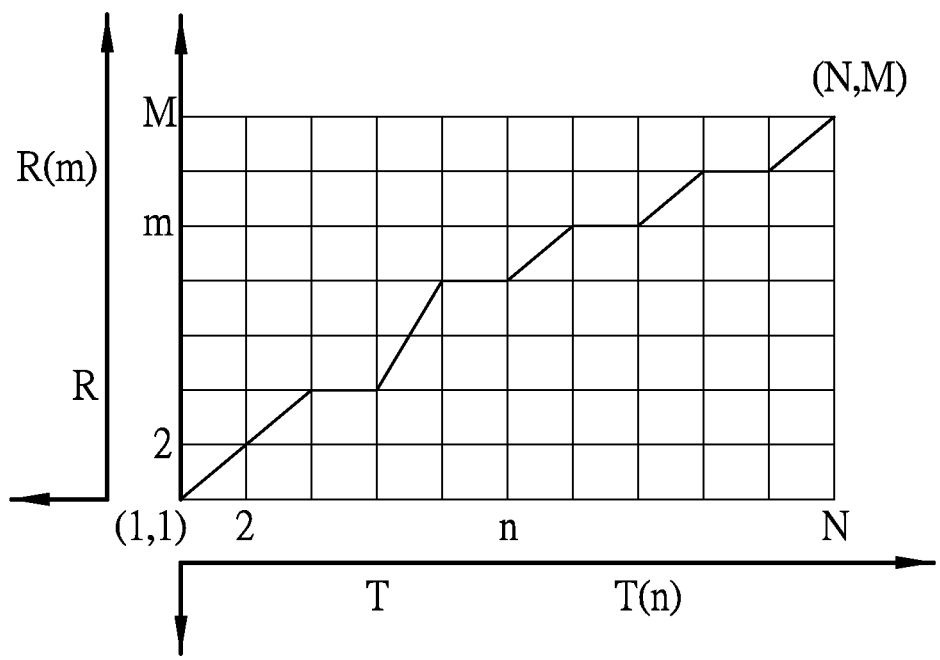
FIG. 10 shows a schematic diagram of the optimal path obtained by utilizing dynamic time warping.

If R represents the reference sample having M sampling points, T represents the test sample having N sampling points, the grids indicated by vertical axis R and horizontal axis T are the intersections (n, m) of the reference sample R and the test sample T. The Euclidean distance can be represented as d[T(n),R(m)], and the summation of the distance cost D can be represented as:

$$D = \sum_{m=1}^{M} d(T(n), R(m)), \text{ referring to FIG. 10.}$$

Figure 11:
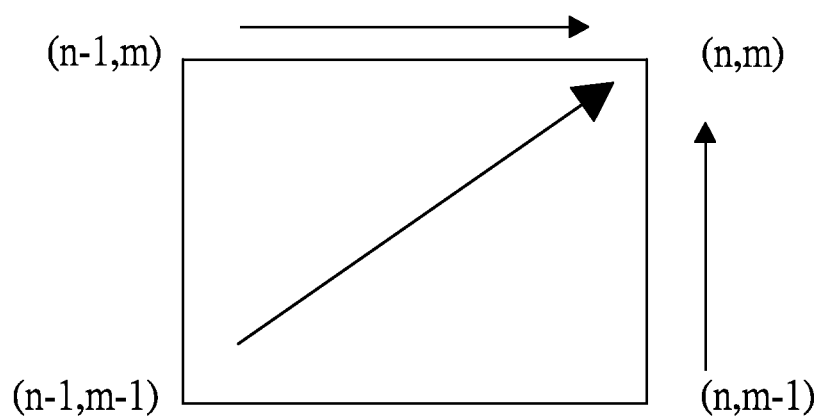
FIG. 11 shows a schematic diagram of the partial best path obtained by the utilizing dynamic time warping.

However, in practical applications, the length of the traces of each input may be different, such that the timeline variance between the test sample and the reference sample is quite large. Thus, the local minimum cumulative cost should be considered. According to the theory of dynamic programming, the value of the local minimum path should be obtained when determining the local minimum path, such that cumulative cost of all cross points in the optimal path can be minimized, referring to FIG. 11. Therefore, D can be $$D(n,m)=\min\{D(n-1,m-1), D(n-1,m), D(n,m-1)\}+d(n,m)$$

The cumulative cost is not arbitrary calculated. First, the sequence of the sample points would not be changed though the speed of the trace may be slow or fast. Then, when obtaining the optimal path, not only must the path be calculated from the first point to the last point for the two time sequences, but also the original sampled time sequence should be maintained.

According to the aforementioned steps S610 to S650, the analysis for the original acceleration information is completed. In the same way, the standard movement information is analyzed in advance. Then, generating the compare result of the similarity of the acceleration information and the standard movement information according to the parameters obtained from the aforementioned analysis. According to the algorithm provided in FIG. 6, the detailed process of the step S140 shown in FIG. 3A about analyzing the acceleration information and comparing the similarity of the acceleration information and the standard movement information should be well understood.

According to above descriptions, the provided body rehabilitation sensing method based on a mobile communication device and a system thereof has the following advantages. First, the sensing module contained in the mobile communication device is directly used for collecting and analyzing the sensed signals (acceleration information), and no additional equipment is required. Second, the wireless network communication technology of the mobile communication device is used to transmit the rehabilitation information (comprising the acceleration information and the user information) to the remote server through the network, for the physiotherapist (or the doctor) to analyze the effectiveness of the rehabilitation. The user does not have to be at a particular place to conduct rehabilitation. Third, the mobile communication device immediately provides the information of the standard rehabilitation movement recorded by the physiotherapist (or the doctor) in advance, such that the user can compare the correctness of his or her movement to improve the efficiency of rehabilitation. Additionally, the mobile communication device allows the user to upload the rehabilitation result to the remote server, for the medical institution to evaluate the efficacy of the treatment quickly. Accordingly, the user does not have to go the outpatient department personally to conduct rehabilitation, and no specific physiotherapist is required to give supervision. This is especially adapted for the user at a remote area. Such that, the trip to the medical intuition of the user for conducting rehabilitation can be avoided and the medical labor force can be saved, to achieve better rehabilitation efficiency.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. A body rehabilitation sensing method based on a mobile communication device, used for the mobile communication device, the mobile communication device having a wireless network module and a sensing module, the method comprising:

the mobile communication device receiving a rehabilitation movement information from a remote server through the wireless network module, and the mobile communication device displaying the rehabilitation movement information by a display module of the mobile communication device;

placing the mobile communication device at a specific portion of the limb of a user;

the sensing module of the mobile communication device executing a correction process;

the sensing module of the mobile communication device sensing the acceleration of the mobile communication device for generating an acceleration information;

the mobile communication device transmitting the acceleration information to the remote server through the wireless network module;

a computing module of the remote server analyzing the acceleration information and comparing the similarity of the acceleration information and a standard movement information; and the remote server transmitting the compare result of the similarity of the acceleration information and the standard movement information to the mobile communication device through the wireless network module;

wherein the correction process comprises:

determining whether the acceleration of the mobile communication device sensed by the sensing module is less than a stability threshold for a time period; and generating an indicating signal which represents the mobile communication device is ready to sense the acceleration of the mobile communication device to generate the acceleration information when the acceleration of the mobile communication device is less than the stability threshold for the time period.

2. The body rehabilitation sensing method based on a mobile communication device according to claim 1, wherein the standard movement information is recorded by the sensing module of the mobile communication device in advance.

3. The body rehabilitation sensing method based on a mobile communication device according to claim 1, wherein after the step of the sensing module of the mobile communication device sensing the acceleration of the mobile communication device for generating the acceleration information, and before the step of the mobile communication device transmitting the acceleration information to the remote server through the wireless network module, the method further comprises:

the mobile communication device generating the indicating signal;

the indicating signal reminding the user to decrease the speed of the movement of the limb when the sensing module senses the acceleration of the mobile communication device exceeds a threshold; and the indicating signal representing the completion of the body rehabilitation movement of the user when the sensing module senses the acceleration of the mobile communication device is less than the stability threshold for the time period.

4. The body rehabilitation sensing method based on a mobile communication device according to claim 3, wherein the indicating signal is sounds, vibrations, emitted light, flashing light, or a display signal displayed on the display module of the mobile communication device.

5. The body rehabilitation sensing method based on a mobile communication device according to claim 1, wherein the sensing module is a triaxial accelerometer, a gravity sensor or a gyroscope.

6. A body rehabilitation sensing system, comprising:

a remote server; and a plurality of mobile communication devices, the mobile communication device having a wireless network module and a sensing module, the communication device utilizing the wireless network module for connecting to the remote server through the network;

wherein the mobile communication device receives a rehabilitation movement information from the remote server through the wireless network module, the mobile communication device displays the rehabilitation movement information by a display module of the mobile communication device;

wherein the mobile communication device is placed at a specific portion of the limb of a user, the sensing module of the mobile communication device executes a correction process, the sensing module of the mobile communication device senses the acceleration of the mobile communication device for generating an acceleration information, the mobile communication device transmits the acceleration information to the remote server through the wireless network module;

wherein a computing module of the remote server analyzes the acceleration information and compares the similarity of the acceleration information and a standard movement information, the remote server transmits the compare result of the similarity of the acceleration information and the standard movement information to the mobile communication device through the wireless network module;

wherein the correction process comprises:

determining whether the acceleration of the mobile communication device sensed by the sensing module is less than a stability threshold for a time period; and generating an indicating signal which represents the mobile communication device is ready to sense the acceleration of the mobile communication device to generate the acceleration information when the acceleration of the mobile communication device is less than the stability threshold for the time period.

7. The body rehabilitation sensing system according to claim 6, wherein the standard movement information is recorded by the sensing module of the mobile communication device in advance.

8. The body rehabilitation sensing system according to claim 6, wherein the mobile communication device generates the indicating signal, the indicating signal is used for reminding the user to decrease the speed of the movement of the limb when the sensing module senses the acceleration of the mobile communication device exceeds a threshold, the indicating signal is used for representing the completion of the body rehabilitation movement of the user when the sensing module senses the acceleration of the mobile communication device is less than the stability threshold for the time period.

9. The body rehabilitation sensing system according to claim 8, wherein the mobile communication device further comprises at least one of a speaker, a vibration generator and a ring signal light module, the indicating signal is at least one of the sounds, vibrations, emitted light, flashing light and a display signal displayed on the display module of the mobile communication device.

10. The body rehabilitation sensing system according to claim 6, wherein the sensing module is a triaxial accelerometer, a gravity sensor or a gyroscope.

* * * * *